(12) United States Patent
Peters et al.

(10) Patent No.: US 9,393,355 B2
(45) Date of Patent: Jul. 19, 2016

(54) BLOOD PUMP

(75) Inventors: Hans-Erhard Peters, Berlin (DE); Joerg Müller, Berlin (DE); Kurt Graichen, Berlin (DE); Peter Nüsser, Kleinmachnow (DE); Manfred Göllner, Berlin (DE); Andreas Arndt, Berlin (DE)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 13/505,368

(22) PCT Filed: Nov. 8, 2010

(86) PCT No.: PCT/EP2010/006863
§ 371 (c)(1),
(2), (4) Date: Aug. 21, 2012

(87) PCT Pub. No.: WO2011/054545
PCT Pub. Date: May 12, 2011

(65) Prior Publication Data
US 2012/0310036 A1 Dec. 6, 2012

Related U.S. Application Data

(60) Provisional application No. 61/258,932, filed on Nov. 6, 2009.

(30) Foreign Application Priority Data

Nov. 6, 2009 (EP) .................................... 09075495

(51) Int. Cl.
A61M 1/12 (2006.01)
A61M 1/10 (2006.01)

(52) U.S. Cl.
CPC .............. *A61M 1/101* (2013.01); *A61M 1/1015* (2014.02); *A61M 1/1017* (2014.02); *A61M 1/1036* (2014.02); *A61M 1/122* (2014.02); *A61M 1/125* (2014.02)

(58) Field of Classification Search
CPC ..... A61M 1/101; A61M 1/125; A61M 1/122; A61M 1/1017

USPC .............. 607/16; 604/16, 151; 623/3.15, 3.13
See application file for complete search history.

(56) References Cited

U.S. PATENT DOCUMENTS

| 4,688,998 A | 8/1987 | Olsen et al. | |
| 5,324,177 A * | 6/1994 | Golding et al. | ............ 417/423.1 |

(Continued)

FOREIGN PATENT DOCUMENTS

| CN | 1372479 A | 10/2002 |
| CN | 1491323 A | 4/2004 |

(Continued)

OTHER PUBLICATIONS

Sinnott et al., "Effect of rotor blade angle and clearance on blood flow through a non-pulsatile axial heart pump", dated Dec. 9-11, 2009, pp. 1-6, Seventh International Conference in CFD in the Minerals and Process Industries, CSIRO, Melbourne, Australia.

(Continued)

*Primary Examiner* — Christopher D Koharski
*Assistant Examiner* — Michael D Abreu
(74) *Attorney, Agent, or Firm* — Brinks Gilson & Lione

(57) ABSTRACT

A blood pump has a hollow body in which an impeller with a spiral blading produces an axial propulsion of blood along the impeller, as well as an at least partly actively stabilized magnetic bearing device and a hydrodynamic bearing device for the impeller. The impeller may be set into a rotation about a rotation axis of the impeller with a motor stator located outside the hollow body. The hollow body has an inlet for the flow of blood into the hollow body in an inflow direction which is essentially parallel to the rotation axis, and an outlet for the outflow of the blood out of the hollow body in an outflow direction which is offset to the rotation axis of the impeller to produce a non-zero outflow angle ($\alpha$) between the inflow direction and the outflow direction. A total artificial heart can be formed from two such blood pumps.

25 Claims, 7 Drawing Sheets

(56) References Cited

U.S. PATENT DOCUMENTS

| | | | |
|---|---|---|---|
| 5,326,344 A | 7/1994 | Bramm et al. | |
| 5,527,159 A | 6/1996 | Bozeman, Jr. et al. | |
| 6,093,001 A | 7/2000 | Burgreen et al. | |
| 6,123,659 A | 9/2000 | le Blanc et al. | |
| 6,227,820 B1 | 5/2001 | Jarvik | 417/423.12 |
| 6,368,083 B1* | 4/2002 | Wampler | 417/423.7 |
| 6,527,699 B1 | 3/2003 | Goldowsky | |
| 6,581,476 B1 | 6/2003 | Fremerey | |
| 6,866,625 B1* | 3/2005 | Ayre et al. | 600/16 |
| 7,070,398 B2 | 7/2006 | Olsen et al. | |
| 8,007,254 B2 | 8/2011 | LaRose et al. | 417/356 |
| 2004/0115038 A1 | 6/2004 | Nuesser et al. | |
| 2007/0100196 A1* | 5/2007 | LaRose et al. | 600/16 |
| 2008/0091265 A1 | 4/2008 | Nuesser et al. | |
| 2009/0118567 A1 | 5/2009 | Siess | |
| 2014/0187852 A1 | 7/2014 | Peters et al. | |

FOREIGN PATENT DOCUMENTS

| | | |
|---|---|---|
| CN | 101282748 A | 10/2008 |
| DE | 196 25 300 A1 | 1/1998 |
| DE | 10 2006 036 948 A1 | 2/2008 |
| EP | 0019313 | 11/1980 |
| EP | 0 060 569 A1 | 9/1982 |
| EP | 0150320 | 8/1985 |
| EP | 0378251 | 7/1990 |
| EP | 1738783 | 1/2007 |
| WO | WO96/31934 | 10/1996 |
| WO | WO 00/64508 | 11/2000 |
| WO | WO 02/066837 A1 | 8/2002 |
| WO | WO2005/030296 | 4/2005 |
| WO | WO 2005/090791 A1 | 9/2005 |
| WO | WO2006/053384 | 5/2006 |
| WO | WO 2007/040663 A1 | 4/2007 |

OTHER PUBLICATIONS

Non-Final Office Action, dated May 6, 2015, pp. 1-22, U.S. Appl. No. 14/115,425, USPTO, Alexandria, Virginia.

* cited by examiner

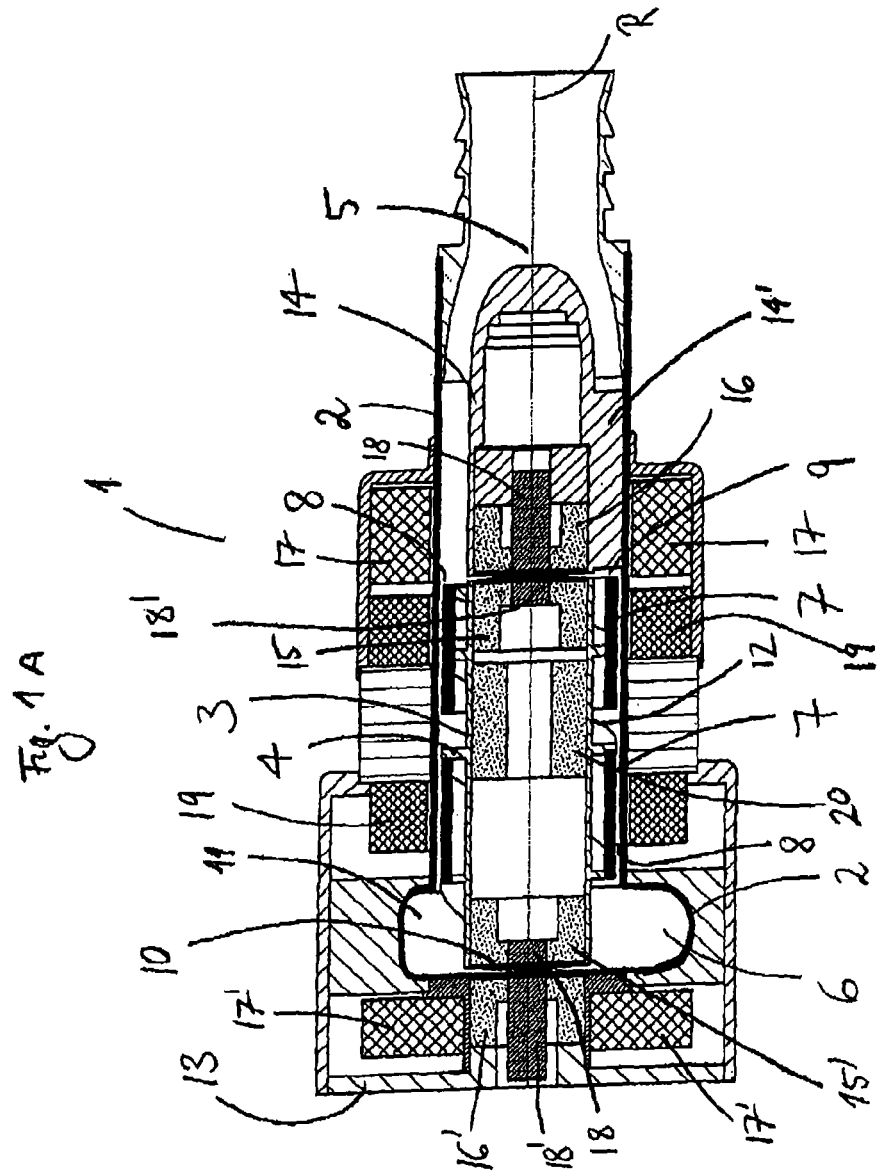

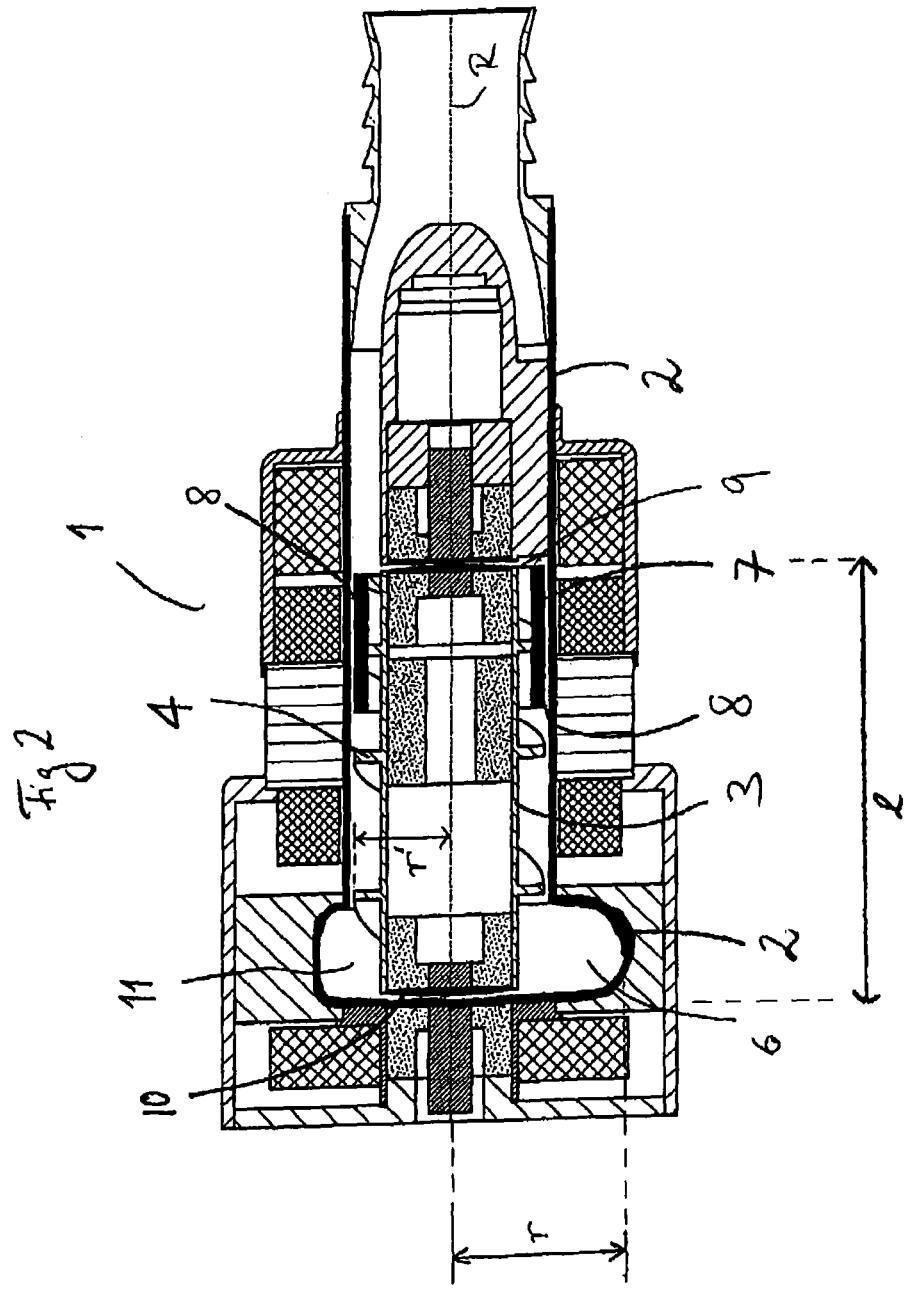

BLOOD PUMP

CROSS-REFERENCE TO RELATED APPLICATIONS

This application is a 371 nationalization of PCT/EP2010/006863, which in turn claims benefit of U.S. Provisional Application 61/258,932 filed Nov. 6, 2009, and European application 09075495.3 filed Nov. 6, 2009.

BACKGROUND

The invention relates to the field of blood pumps.

A blood pump here and hereinafter is to be understood as a pump which serves for supporting or creating a blood flow within a human or animal body and is suitable for implantation into the thorax of a human or animal, outside the heart. With left ventricular assist devices (LVAD), a connection exists between the left heart half and an inlet of the blood pump as well as between the outlet of the blood pump and the aorta departing from the heart, for the support or creation of the blood circulation through the body (systemic circulation). With right ventricular assist devices (RVAD) there exists a connection between the right heart half and the pulmonary artery stem which leads to the left and to the right pulmonary artery, (or a direct connection between the RVAD and the left and/or right pulmonary artery) for the support or creation of the blood circulation through the lung (pulmonary circulation). The blood, within the blood pump, is led through a hollow body which is part of a pump housing or is arranged in such a pump housing. A rotating impeller, with a blading for producing a pressure and a flow of the blood resulting therefrom, is provided in the hollow body. So-called total artificial hearts (total heart pumps) contain a left ventricular and a right ventricular assist device (blood pump) for the support or the creation of the complete blood circulation. Flexible connection tubes or connection pipes as well as, as the case may be, flow bends or elbows, are applied for creating the mentioned connections between the blood pump and the heart or blood vessels. Moreover, at least one cable line is necessary for the energy supply and, as the case may be, for the control of the blood pump, said cable line connecting the blood pump to an energy storer and, as the case may be, to a control unit.

A main problem with the implantation and the use of such blood pumps, in particular total artificial hearts, is the spatial requirement of such blood pumps and the flexible connection tubings as well as the cable line in the thorax space in the vicinity of the heart.

A further difficulty lies in the danger of destruction of the blood cells (hemolysis) due to the blood pump, in particular at the mechanical bearings of the impeller, narrowings and abrupt changes in direction of the blood flow through the blood pump, as well as by way of large pressure gradients within the blood pump. With the design of blood pumps, for this purpose, often mechanical bearings of the impeller are replaced by a magnetic and/or hydrodynamic bearing.

An additional problem lies in the fact that a significantly smaller blood pressure needs to be created for the pulmonary circulation, than for the systemic circulation, wherein however the same blood volume per time needs to be transported through both blood circulations. The blood pressure produced by the blood pump depends on the rotational speed of the impeller of the blood pump. It has been found to be difficult to design a pump which is suitable for setting very different values of the blood pressure within a range of about 5 mmHg up to about 150 mmHg with a stable, constant volume flow between 0 l/min to 20 l/min adapted to the physiological conditions, and which in this manner may be applied as an RVAD as well as an LVAD, or which is suitable for the design of a total artificial heart.

It is therefore the object of the present invention, to suggest a blood pump as well as a total artificial heart, which solves or at least reduces the problems mentioned above. A corresponding blood pump or total artificial heart should thus have an as low as possible spatial requirement and be suitable for the support or creation of blood pressure, in a manner which as gentle as possible to the blood. Moreover, it should be suitable for covering a large range of the blood pressure with an as suitable as possible volume flow.

SUMMARY

A blood pump according to the invention comprises a hollow body, in which an impeller with a blading is provided, for the production of an axial propulsion of the blood along the impeller, as well as at least partly actively stabilised magnetic bearing device and a hydrodynamic bearing device for the impeller, wherein the impeller may be set into a rotation about a rotation axis of the impeller, with a motor stator located outside the hollow body, and wherein the hollow body comprises an inlet for the flow of blood into the hollow body in an inflow direction essentially parallel to the rotation axis, and an outlet for the flow of the blood out of the hollow body in a flow-out direction, wherein the outlet is arranged offset with respect to the rotation axis of the impeller for producing an outflow angle between the inflow direction and the outflow direction, which is different from zero.

Thereby, an outlet is to be understood as an opening in a wall of the hollow body, wherein the outlet as a rule is led further to the outside by a connection union.

The invention is based on the concept of achieving an as small as possible spatial requirement of the blood pump, including the necessary flexible connection tubes, by way of the angle between the inflow direction of the blood and the outflow direction of the blood being different from zero, wherein by way of a suitable selection of this angle, the outlet of the implanted blood pump may be aligned in the direction of the blood vessel, to which the blood pump is to be connected, thus for example the aorta, the pulmonary artery stem or another blood vessel. In this manner, one may select a particularly short flexible connection tubing between the blood pump and the blood vessel, since the flexible connection tubing may be lead in an as straight-lined as possible manner and in a direct path, to the blood vessel and not along a curvature forming a detour. Moreover, the application of flow bends or elbows for deflecting a flow direction of the blood as a rule thus becomes superfluous. This angle preferably lies in a range of between 30° and about 150°, particularly preferably in a range between about 75° and about 105°, wherein with a given angle of 90° the blood leaves the blood pump at a right angle to the rotation axis, and with a given angle of 0° the outflow is effected in the axial direction.

With the application of conventional axial blood pumps, as a rule, greatly curved flexible connection tubings are necessary, since conventional axial blood pumps always have an axial outlet (i.e. the angle between the inflow direction and the outflow direction of the blood is about 0°).

The basic principle of an axial propulsion of the blood by the impeller is retained by the blood pump according to the invention. This is advantageous, since those blood pumps which are also indicated as axial pumps and which mainly exert an axial force effect on the blood and thus accelerate this mainly axially, thus in the direction of the rotation axis along the impeller, deliver the blood in a particularly gentle manner.

In comparison to this, so-called radial pumps accelerate the blood mainly radially to the rotation axis of the impeller. Radial pumps moreover mostly have a radial outlet, which often entails the advantage of particularly short connections to blood vessels.

The blood pump according to the invention which is suggested here, thus unifies the advantage of an axial pump with regard to the gentle delivery of blood, as well as the advantage of a radial pump with regard to the shorter flexible connection tubes between the blood pump and the blood vessels and thus with regard to a small spatial requirement as well as improved rotor dynamics.

For generating the axial propulsion of the blood according to the invention the blading of the impeller is designed as a spiral (helix). Such a spiral-shaped blading may by single-start or multi-start. Thus, the spiral can comprise one or more, preferably two to six, individual spiral-shaped, i.e. helical, blades (vanes). Each of these blades of the blading may revolve partially, completely or several times around the impeller with respect to the rotational axis of the impeller. Preferably, the individual blades are wound at least once, more preferably at least one and a half time around the impeller. Furthermore, the surfaces of the at least one blade of the spiral pointing downstream and the rotational axis of the impeller enclose a non-zero angle (blade angle). The blade angle is related to the pitch and the lead of the blading. Analogously to common screw thread nomenclature, the pitch of the blading is defined as the axial distance between two neighboring windings of a blade if the blading is a single-start blading, and as the axial distance between two neighboring blades if the blading has two or more individual blades. The respective distances mentioned above are always measured between surfaces of the blades or blade windings facing in the same axial direction (and not facing towards each other). Accordingly, the lead of the blading of the impeller may be defined as the axial distance a volume element of blood adjacent to a blade of the blading is axially advanced when the impeller is turned one revolution (neglecting any tangential movements of said volume element for simplicity). In order to determine the pitch and the lead at the axial ends of the blading, the blading may be extrapolated in axial direction. In the special case of a constant pitch the lead of an N-start spiral-shaped blading equals the pitch times N.

By modifying the local blade angle, the pitch and the lead of the blading, the transport effect of the blading on the blood can be adjusted. The blade angle, the pitch as well as the lead may vary along the axial extent (length) of the impeller. The blade angle, pitch or lead at a given axial position of the impeller is therefore referred to as local blade angle, local pitch or local lead, respectively.

Preferably, the local pitch of the blading along an entire axial extent of the blading lies in a range between 2 mm und 20 mm, more preferably in a range between 3 mm und 15 mm. The local pitch of the blading along the entire axial extent of the blading preferably lies in a range between 2 mm und 120 mm, more preferably in a range between 3 mm und 40 mm. The local blade angle along the entire axial extent of the blading preferably lies in a range between 80° and 20°, more preferably in a range between 70° and 30°.

The local pitch and the local lead may increase from an upstream side of the blading to a downstream side of the blading. At the upstream side, the local pitch may lie in a range between 2 mm and 8 mm and on the downstream side between 10 mm and 20 mm. At the upstream side, the local lead may lie in a range between 2 mm and 50 mm and on the downstream side between 10 mm and 120 mm. Preferably the local pitch and the local lead increase monotonously from the upstream side to the downstream side of the blading. The blade angle at the upstream side is preferably in a range between 80° and 45°, more preferably between 75° and 55°. The blade angle at the downstream side of the blading is preferably in a range between 70° and 35°, more preferably between 60° and 40° Preferably the blade angle decreases monotonously from the upstream side to the downstream side of the blading.

Averaging the local pitch, the local lead and the blade angle along the axial extent of the blading yields the average pitch, the average lead and the average blade angle, respectively. Preferably, the average pitch lies in a range between 5 mm and 12 mm and the average lead in a range between 5 mm and 85 mm. Moreover, the average blade angle preferably lies in a range between 45° and 65°.

According to the invention, the blood pressure build not only results from pushing the blood axially forward via the blading, but additionally also by transferring a tangential flow velocity and with it rotational energy onto the blood. Generally, the tangential flow velocity of the blood and the amount of rotational energy transferred onto the blood via the blading increases with increasing pitch and lead and with decreasing blade angle.

In the special embodiments shown in the figures below, the blading extends into the spiral housing of the blood pump. Since the outflow of blood from the spiral housing (volute) runs tangentially to the impeller, the above mentioned tangential velocity component of the blood is efficiently used for building up the pressure.

The individual spiral-shaped blades of the blading are preferably designed continuously along the length of the impeller. Furthermore, the blading preferably spreads over at least 80% of the axial extent (length) of the impeller, more preferably over at least 90% of the length of the impeller and most preferably over the total length of the impeller. In this way, the impeller is particularly suitable for producing a gentle, low-turbulence axial propulsion of the blood.

Preferably, an outer contour of the spiral is designed in a cylinder-shaped manner. Furthermore, also a peripheral surface of the impeller, which carries the blading of the impeller between the upstream-side and the downstream-side, may by essentially cylinder-shaped, truncated cone-shaped or cone-shaped. It can also be envisaged to vary the height of the blading along the impeller, preferably to increase the height inside the spiral housing. Moreover, the impeller is preferably elongated in direction of the rotational axis. Preferably, the impeller has a maximal total diameter (including the blading and measured perpendicularly to the axis of rotation) which is not larger than 60% of the axial extent (length) of the blading of the impeller, more preferably not larger than 30% of the axial length of the blading of the impeller. An elongated form of the impeller allows for a particularly slim shape of the blood pump.

In one embodiment, it is envisaged that a maximal radial extent of the blading, i.e. a maximal height of the blading, is smaller than 50% of a maximal total radius of the impeller (measured perpendicularly to the axis of rotation and including the blading), preferably the maximal height of the blading is smaller than 30% of the maximal total radius of the impeller. Typically, the maximal height of the blading lies in a range between 1 mm und 4 mm, more preferably in a range between 1.5 mm und 3 mm.

The at least one blade of the blading may have a maximal width (measured perpendicularly to the rotational axis and perpendicularly to the height of the blading) which is smaller than 10% of a maximal total circumference of the impeller (measured perpendicularly to the axis of rotation and including the blading), preferably the maximal width is less than 5% of the maximal total circumference of the impeller. Typically, the maximal width lies in a range between 0.5 mm and 3 mm, preferably between 1 mm und 2 mm. In this manner, the at least one blade has the form of thin helical rib.

The blood pump according to the invention is further characterised by the omission of an outlet guide vane which is mounted downstream of the impeller in the flow direction. Such a downstream guide vane in common axial pumps with an axial outlet, serves for converting rotation movements of the blood into an additional axial pressure build-up and thus for an efficiency increase of the axial delivery of the blood. With the non-axial outlet according to the invention, the rotational movement of the blood at least partly also contributes to the blood pressure which is produced by the blood pump, which may advantageously also be utilised by way of omitting the downstream guide vane. Moreover, the mechanical loading of the blood by way of a deflection of the blood by the downstream guide vane is avoided by way of omission of the downstream guide vane, by which means the danger of damage to the blood is further reduced.

A further significant advantage which is achieved by way of omitting the downstream guide vane lies in a smaller axial length of the blood pump and thus in a reduced spatial requirement of the blood pump.

Moreover, the problem of unfavourable onflow angles of the downstream guide vane at certain operating points of the blood pump is also done away with due to the omission of the downstream guide vane. If specifically the downstream guide vane is subjected to onflow at an unfavourable angle, then even pressure losses may arise due to the downstream guide vane. Moreover, local pressure fluctuations may be formed at the downstream guide vane, which have an unfavourable effect on the flow course of the blood on the impeller and render a stable bearing of the impeller more difficult, in particular with lower rotational speeds.

An at least partly actively stabilised magnetic bearing device for the impeller, as is described for example in WO 00/64030, is basically suitable for the contact-free accommodation of radial as well as axial forces. In particular, an active stabilisation of the axial bearing (active axial stabilisation) has been found to be particularly advantageous with all rotational speeds. The magnetic bearing device may comprise permanent-magnetic elements integrated into the impeller for the purpose of an active axial stabilisation (the impeller as a rule also contains permanent-magnetic elements for the functioning as a motor rotor of an electric motor). Additionally, the magnetic bearing system may comprise ring coils for an active axial stabilisation, which permit an active stabilisation (closed-loop control) of the axial position of the impeller by way of an axial magnet flux. These ring coils are independent of a motor winding and serve exclusively for the actively stabilised, axial bearing of the impeller. The mentioned ring coils may for example be arranged outside the hollow body such that they surround these in an annular manner. Moreover, the magnetic bearing device may comprise a sensor system for measuring a position of the impeller, in particular for ascertaining a deviation from an axial desired position, as well as a closed-loop control unit which is connected to the sensor system and the ring magnets and which sets the magnetic flux produced by the ring magnets, according to the measured axial position of the impeller, for correcting a possible deviation of the impeller from the desired position. Further details are to be deduced for example from the above mentioned document or the description of special embodiments of the invention further below.

In a further development, the magnetic bearing device of the blood pumps moreover comprises permanent-magnetic bearing elements for a passive radial bearing (passive radial stabilisation) of the impeller. These permanent-magnetic bearing elements may for example be arranged within the hollow body in the direct vicinity to an upstream-side or a downstream-side of the impeller, for example in a hub or the impeller, a guide vane or a termination plate of the hollow body. Further details are to be deduced again from the mentioned document or the description of special embodiments of the invention further below.

The hydrodynamic bearing of impellers in blood pumps is basically known. In one embodiment of the invention, one envisages the hydrodynamic bearing device of the impeller as in WO 02/66837 being realised by a support ring connected to the impeller or several such support rings and, in this manner, forming an annular gap (or several annular gaps) between the support ring and an inner wall of the hollow body, for a radial bearing of the impeller. Such a support ring, preferably formed as a rotationally-symmetrical hollow cylinder, may be designed in different widths and may be fastened on the impeller at any location, in order to achieve an optimal stabilisation of the impeller, in particular with respect to tilting of the impeller. In this manner, one may compensate hydrodynamic and mechanical imbalances of the impeller in a particularly effective manner. This is particularly advantageous, if as is described further below, a (spiral-shaped) discharge channel is partly peripheral around the impeller. In this case, a suitable support ring directly upstream of the discharge channel in the flow direction, may contribute to a stabilisation of the impeller.

A further development of the invention envisages the outlet of the hollow body being arranged between an upstream-side of the impeller, said upstream-side being away from the inlet, and a downstream-side of the impeller, said downstream-side being away from the inlet. In this manner, one may realise particularly compact embodiments with a reduced construction length. Moreover, it has been found that this contributes to particularly good flow characteristics of the blood pump and thus also to a stabilisation of the impeller, by which means the pressure region which may be covered by the blood pump is increased. Preferably, the outlet is arranged in a direct environment of the downstream-side of the impeller, in order to utilise as much as possible the actual propulsion due to the blading of the impeller which is preferably bladed over an entire length of its peripheral surface. In order to increase this, the blading of the impeller preferably also extends along the outlet, i.e. at the height of the outlet.

In a further development, the blood pump comprises a backing plate which is arranged essentially perpendicular to the rotation axis of the impeller, for terminating the hollow body. In the case that the outlet, as described above, is arranged between the upstream-side and the downstream-side of the impeller, this backing plate is preferably arranged in the direct vicinity of the downstream-side of the impeller, in order thus to avoid flow-free dead spaces between the impeller and the backing plate. Such dead spaces generally entail an increased risk of blood clots and are therefore to be avoided as much as possible. In a further development, the backing plate is designed as a closure which is easy to open, for the simple creation of an axial access into the hollow body, such as for a simpler assembly or an adjustment of the blood pump during the assembly process.

In one embodiment, one envisages an inner radius of the hollow body being enlarged for forming a discharge channel which runs tangentially around the impeller and runs into the outlet (spiral housing). Such a discharge channel permits a discharge of the blood through the outlet out of the hollow body, essentially tangential to the impeller (more precisely tangentially to a peripheral surface of the impeller). In this manner, a respective tangential flow component of the blood and the kinetic energy of the blood which this entails, are retained particularly well and in a low-loss manner on flowing out of the hollow body and may be utilised for the efficient production of the blood pressure. A flow component of the blood which runs tangentially to the peripheral surface but perpendicularly to the rotation axis, in principle always arises with axial pumps, since the propulsion produced by the impeller, apart from the axial component, also has a component perpendicular to the rotation axis. In particular, eddies with corresponding energy losses as may occur with a simple radial outlet, are avoided by way of such a discharge channel. Moreover, in this manner, the flow characteristics of the blood pump are improved and thus also the stability of the impeller, by which means the pressure range which may be covered by the blood pump is further increased. Moreover simultaneously, the mechanical loading of the blood which the mentioned eddies entail, may be largely avoided.

In order to achieve an as high as possible efficiency of the blood delivery with an as compact as possible construction shape, the blading of the impeller also extends along the discharge channel, i.e. at a height of the discharge channel.

A further development envisages the discharge channel being widened towards the outlet and thus being designed in a spiral manner like a spiral housing. In this manner, a continuous reduction of the flow speed (with a constant volume flow) towards the outlet, and a reduction of eddy formations is achieved, and thus a particularly gentle flow of the blood out of the hollow body. Moreover, the pressure increase produced by the blood pump, at the outlet in the transition to the outlet channel, may be transmitted in a particularly effective manner by way of the reduced flow speed of the blood. Typical flow speeds at the outlet of the blood pump in this example lie of the magnitude below 1 m/s.

In a further embodiment, one envisages a peripheral surface of the impeller, which carries the blading of the impeller between the upstream-side and the downstream-side, being essentially cylinder-shaped, truncated cone-shaped or cone-shaped, for the production of as uniform and eddy-free as possible propulsion. In this manner, a mainly axial propulsion is ensured, thus a propulsion which is gentle with regard to the blood. However, one may also achieve an additional radial acceleration component by way of a diameter of the impeller which increases towards the downstream-side of the impeller.

In particular, in combination with a cylinder-shaped or truncated-cone-shaped design of the impeller, one may envisage an inlet guide vane which is arranged on the upstream-side of the impeller. This inlet guide vane on the one hand serves for an as eddy-free as possible onflow of the impeller, thus an onflow which is gentle to the blood and is as loss-free as possible, and may furthermore comprise a stationary blading, in order to reduce the rotation movement of the blood about the rotation axis of the impeller and convert it into an axial propulsion for further increasing the delivery output of the blood pump. Preferably, the inlet guide vane is arranged in the direct vicinity to the upstream-side of the impeller, for avoiding or reducing a non-flow dead space between the inlet guide vane and the impeller. Moreover, the inlet guide vane, as already described, may contain permanent-magnetic bearing elements which are components of the magnetic bearing device.

In a further development, one envisages the blood pump comprising a control unit which is set up to set rotational speeds of the impeller in a range between 3000 rpm and 35000 rpm, for producing a blood pressure at the outlet in a range between 5 mmHg and 150 mmHg with a volume flow of the blood which is adapted to requirements. In this manner, a volume flow between 0 l/min and 20 l/min may be set depending on the flow resistance of the pulmonary circulation or the systemic circulation.

An alternative blood pump comprises a hollow body, in which an impeller is provided with a blading, for producing an axial propulsion of the blood along the impeller, wherein the impeller may be set into rotation about a rotation axis of the impeller with a motor stator which is located outside the hollow body, and wherein the hollow body comprises an inlet for the flow of blood into the hollow body in an inflow direction which is essentially parallel to the rotation axis, and an outlet for the flow of the blood out of the hollow body in an outflow direction, wherein the outlet is arranged offset with respect to the rotation axis of the impeller, for producing an outflow angle between the inflow direction and the outflow direction, which is different from zero, wherein an inner radius of the hollow body is enlarged for forming a spiral-shaped discharge channel which runs tangentially around the impeller and which runs out into the outlet, for the flow of the blood out of the hollow body, said flow running essentially tangentially to the impeller, wherein the outlet of the hollow body is arranged between an upstream-side of the impeller, said upstream-side facing the inlet, and a downstream-side of the impeller, said downstream-side being away from the inlet.

Such a blood pump may contain a mechanical, hydrodynamic, a magnetic or a hybrid bearing device, for bearing the impeller. Moreover preferably a peripheral surface of the impeller, which carries the blading, may be designed in an essentially cylinder-shaped manner for an axial propulsion of the blood.

All technical features which are specified and described above are to be considered for the further development of this alternative blood pump. The mentioned advantages arise in each case. For the sake of completeness, the features are one again cited in a brief manner. The embodiments further above are referred to for a more detailed explanation.

Thus the hydrodynamic bearing device of the impeller may be designed as a support ring connected to the impeller, for the formation of an annular gap between the support ring and an inner wall of the hollow body. It is also possible for the outlet of the hollow body to be arranged between an upstream-side of the impeller, said upstream-side facing the inlet, and a downstream-side of the impeller, said downstream-side being away from the inlet. One may also envisage an inner radius of the hollow body being enlarged for the formation of a discharge channel which runs tangentially around the impeller and runs out into the outlet, for the flowing-away of the blood out of the hollow body, which is essentially tangential to the impeller. Moreover, it is possible for this discharge channel to widen towards the outlet.

Moreover, one may envisage the magnetic bearing device comprising an actively stabilised axial bearing.

Furthermore, it is possible for a peripheral surface of the impeller, which carries the blading, being designed in a cylinder-shaped, cone-shaped or truncated-cone-shaped manner. The blading of the impeller may be designed as a spiral. Also all features concerning the shape of the blading, the blades of the blading and of the impeller as described above may be realized with this alternative blood pump.

Moreover, one may envisage an inlet guide vane, which may include parts of the magnetic bearing device.

Finally, the blood pump may comprise a control unit which is set up to set rotational speeds of the impeller in a range of between 3000 rpm and 35000 rpm for producing a blood pressure at the outlet in a range between 5 mmHg and 150 mmHg with a volume flow which is adapted to physiological conditions.

In a total artificial heart according to the invention, one envisages providing two blood pumps of a type suggested here, wherein a first blood pump is preferably used as an LVAD and a second blood pump as an RVAD. The total artificial heart is particularly space-saving and may thus be arranged in the thorax at the heart in a particularly simple manner by way of the application of the blood pumps described here.

In one embodiment, one envisages the impellers of both blood pumps of the total artificial heart being arranged on a common rotation axis, by which means a particularly simple design and assembly is made possible. Moreover, this permits an advantageous slim shape of the total artificial heart, by which means an implantation in the thorax is simplified.

In one embodiment example, the impellers of both blood pumps are fixedly connected to in another into a single, common impeller, wherein the cavities of both blood pumps are grouped together into a common hollow body (housing). This permits a construction of the total artificial heart pump which is particularly short axially. Moreover, a simple bearing is possible in this manner, since the common impeller has less degrees of freedom than two individual impellers.

In a further embodiment example, one envisages a bearing block being present between the impeller of the first blood pump and the impeller of the second pump, in which bearing block at least parts of the bearing device of the first and/or second blood pump are integrated.

BRIEF DESCRIPTION OF THE DRAWINGS

Special embodiments of the invention are described hereinafter in more detail by way of FIGS. 1A, 1B, 2-6. The same reference numerals indicate the same features with regard to subject-matter. There are shown in.

DESCRIPTION OF PREFERRED EMBODIMENTS

Figure 1B:
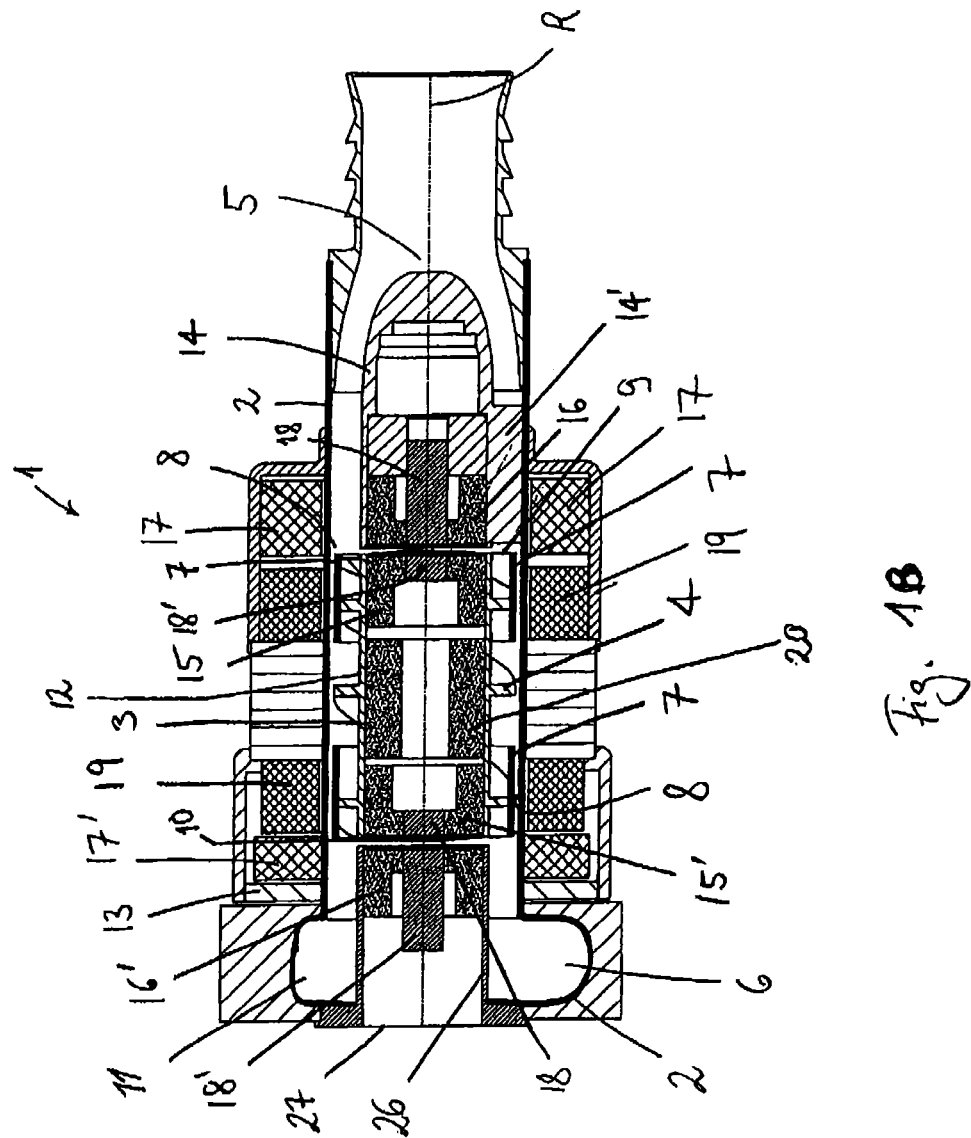
FIG. 1A a schematic representation of a longitudinal section through a blood pump of the type suggested here, FIG. 1B a schematic representation of a longitudinal section through a blood pump of the type suggested here, FIG. 2 a schematic representation of a longitudinal section through a blood pump of the type suggested here, FIG. 3 a schematic representation of a cross section through a hollow body of a blood pump of the type suggested here, FIG. 4 a schematic representation of a partly cutaway hollow body of a blood pump of the type suggested here, FIG. 5 a schematic representation of a total artificial heart of the type suggested here, with a single impeller and FIG. 6 a schematic representation of a total heart pump of the type suggested here, with two individual impellers.

A schematic representation of a longitudinal section through a blood pump 1 of the type suggested here is represented schematically in FIG. 1A. The blood pump 1 comprises a hollow body 2 (represented as a continuous thick line), in which an impeller 3 with a blading 4 is provided. Moreover, the hollow body 2 comprises an inlet 5 for the flow of blood in an inflow direction which is parallel to a rotation axis R (shown dashed), and an outlet 6 for the outflow of blood in an outflow direction which runs perpendicular to the section plane. Accordingly, in this embodiment example, the outlet is arranged offset at a right angle relative to the rotation axis R, for producing an outflow angle $\alpha$ of $\alpha=90°$, which is different from zero, between the inflow direction and the outflow direction.

The outlet 6 of the hollow body 2 is arranged between an upstream-side 9 of the impeller 3, said upstream-side facing the inlet, and a downstream-side 10 of the impeller 3, said downstream-side being away from the inlet. An inner radius of the hollow body 2 serves for forming a discharge channel 11 which runs tangentially around to the impeller 3 and runs out into the outlet 6, for a discharge of the blood out of the hollow body 2, said discharge running essentially tangentially to the impeller 3.

Moreover, a hydrodynamic bearing device is provided which is designed as two support rings 7 connected to the impeller 3, for the formation of two annular gaps 8 between the support rings 7 and an inner wall of the hollow body 2, for a radial bearing of the impeller 3.

A peripheral surface 12 of the impeller 3, which carries the blading 4, is formed in a cylinder-shaped manner, but may just as well be designed in a truncated-cone-shaped or cone-shaped manner. The axial dimension (length) L of the impeller is selected larger than a diameter D of the impeller on the downstream-side of the impeller. The blading of the impeller is characterised by a pitch which increases towards the outlet 6. In this manner one permits an axial propulsion up to the discharge channel 11, which is particularly gentle to the blood. The blading of the impeller 4 extends axially completely (in other embodiments partly or not at all) into the discharge channel 11 and the outflow 6.

An inlet guide vane 14 which is provided with a blading 14', is provided in the direct vicinity of the upstream-side 9 of the impeller 3.

The blood pump further comprises a partly actively stabilised bearing device which contains an actively stabilised, magnetic axial bearing as well as a passive, magnetic radial bearing. The magnetic bearing device firstly comprises two permanent magnets 15, 15' which are arranged in the impeller at the upstream-side and at the downstream-side. Furthermore, two further permanent magnet bearings 16, 16' which are poled opposite to these (attracting) and which are integrated into the inlet guide vane 14 and the backing plate 13, respectively, serve the formation of the passive, magnetic radial bearing, which ensures that the impeller 3 is held in a radial desired position between the inlet guide vane 14 and the backing plate 13. Moreover, for the actively stabilised magnetic axial bearing, two ring coils 17, 17' are arranged outside the hollow body 2, in front of and behind the impeller 3, such that they are peripheral around the hollow body 2 in an annular manner for producing an axial magnetic flux. Moreover, the magnetic bearing device comprises a sensor system which comprises distance sensors 18, 18' integrated into the inlet guide vane 14 and/or the backing plate 13 as well as into the impeller 3, for measuring the gap widths between the impeller 3 and the inlet guide vane 14 or the backing plate 13, as well as a closed-loop control unit (not shown here) which is connected to the distance sensors 18, 18' and the ring magnets, said closed-loop control unit setting the magnet flux produced by the ring magnets, according to the measured axial position of the impeller, for correcting a possible deviation of the impeller from an axial desired position.

Finally, a motor winding 19 running around the hollow body and a motor magnet 20 integrated into the impeller are provided, said motor magnet being magnetised in an alternating radial manner, for driving the impeller 2.

In FIG. 1B, a schematic representation of a longitudinal section through a blood pump 1 of the type suggested here is shown, which differs from the blood pump described by way of FIG. 1A in that a central, cylindrical rod 16 extends from a downstream-side 27 of the pump 1 axially into the hollow body 2 towards the impeller 3. In said rod 26, one of the distance sensors 18' is integrated for measuring the gap width between the impeller 3 and the rod 26 as well as one of the permanent magnet bearings 16' being a part of the passive, magnetic radial bearing. Furthermore, the ring coil 17' of the actively stabilized axial bearing now is positioned axially before the outlet 6 and runs around the hollow body 2, while in the embodiment shown in FIG. 1A, the respective ring coil 17' is located behind the hollow body 2 (with respect to the axial pump direction) and consequently does not run around the hollow body 2. All other features of the embodiment shown in FIG. 1B are identical to the features of the embodiment shown in FIG. 1A.

In FIG. 2, a schematic representation of a longitudinal section through a blood pump 1 of the type suggested here is shown, which differs from the blood pump described by way of FIG. 1A only by way of a changed hydrodynamic bearing device. In the example shown in FIG. 2, this is designed as a single support ring 7 connected to the impeller 3, for forming an individual annular gap 8 between the support ring 7 and an inner wall of the hollow body 2, for a radial bearing of the impeller 3

Moreover, a radius r of the hollow body 2 at a height of the discharge channel 11 is represented, wherein this radius increases towards the outlet, for forming a spiral-shaped discharge channel 11 which widens towards the outlet. A radius of the impeller blading is indicated as r'. It is the case that r'<r.

For the embodiment shown, it is r'=8 mm and r=14 mm. Furthermore, the impeller is elongated, having an axial extent (length) of 40 mm. The blading is spread over the entire length 1 of the impeller 3 so that the axial extent of the blading 4 is also 40 mm. The maximal total diameter of the impeller 3 is given by 2r'=16 mm, which is less than 50% of the axial blading extent.

The blading 4 of the impeller 3 consists of 2 blades 4 (two-start blading) each of them having a maximal height of 2 mm, which is less than 30% of the maximal total impeller radius r'. The maximal width of the blades 4 is 1.5 mm which is less than 5% of the maximal total circumference of the impeller 3 (given by 2πr'=52.27 mm). Moreover, the blades 4 each run about 1.8 times around the impeller 3 (with respect to the rotational axis R).

At the upstream-side 9 of the impeller 3, a local pitch of the blading 4 is about 5 mm and a local lead is about 12 mm. The local pitch and the local lead monotonously increase towards the downstream-side 10 of the impeller 3 to a pitch value of about 12 mm and a lead value of about 40 mm at the downstream-side 10 of the impeller 3, respectively. On average the pitch is about 10 mm and the lead is about 30 mm. At the upstream-side 9 of the impeller 3, a blade angle of the blades is about 75° and monotonously increases towards the end 10 of the impeller to a value of about 45°. On average the blade angle is about 60°.

Note that the explicit values given above for quantifying the design of the impeller, the blading and other parts of the blood pump shown in the figures only serve for illustrative purposes and by no means are restrictive. All parts of the blood pump can be modelled and reshaped to achieve desired pump characteristics. Preferred ranges for various parameters of the pump design are given further above in the general part of the description.

Figure 3:
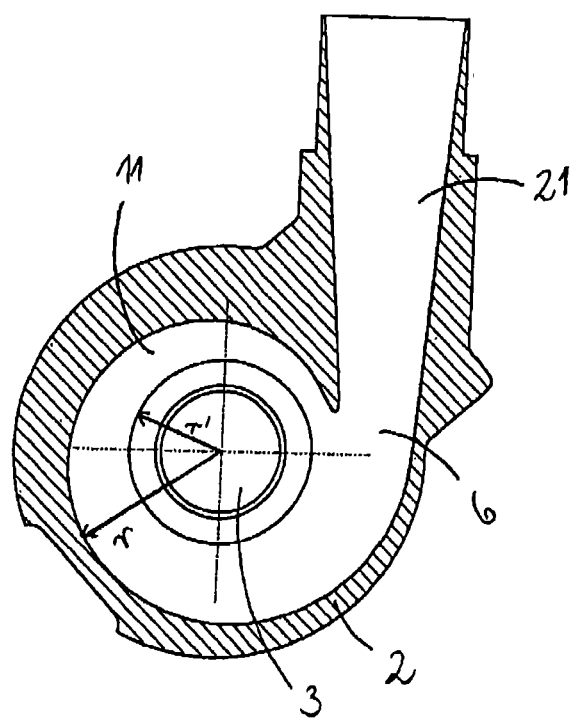

FIG. 3 shows a schematic representation of a cross section through a hollow body 2 of a blood pump 1 according to FIG. 1A or FIG. 2. The cross section runs perpendicularly to the rotation axis R through the discharge channel 11 of the hollow body 2 of the blood pump 1. The hollow body 2 has a radius r which in comparison to a radius r' of the hollow body is increased to a height of the upstream-side 3 of the impeller 3, for forming the discharge channel 11. The discharge channel 11 widens in a spiral-like manner in its course towards the discharge 6 and in this manner forms a spiral housing. The discharge 6 is continued to the outside into a connection union 21, which is widened further to the outside for reducing the flow speed of the blood.

Figure 4:
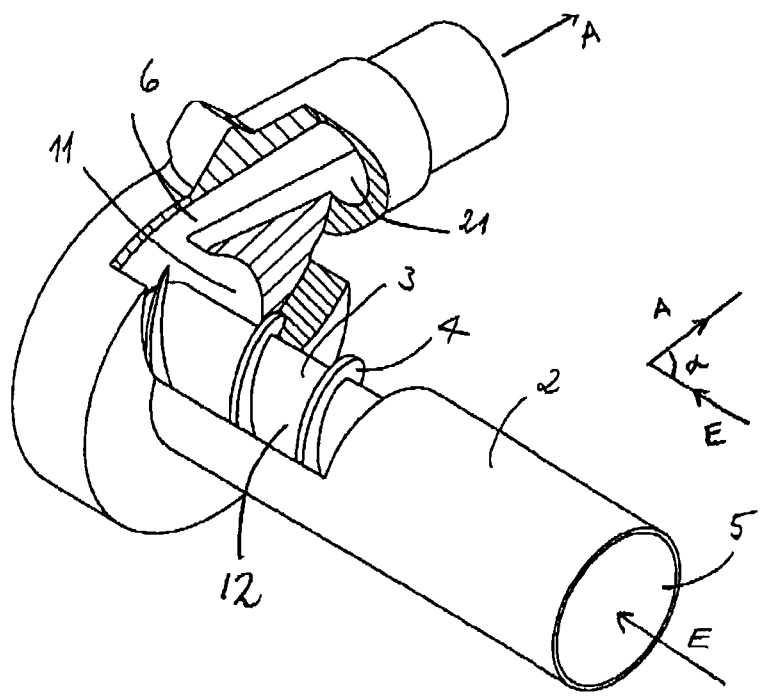

FIG. 4 shows a schematic representation of a partly cut-away hollow body 2 of a blood pump 1 according to FIG. 3. Again, one may recognise the hollow body 2 with the inlet 5 for the inflow of blood in an inflow direction which is indicated by the arrow indicated at E, with a tangential outlet 6 which is lengthened into an outlet union 21, for the outflow of the blood in an outflow direction which is indicated by the arrow indicated at A and which runs at a right angle to the inflow direction E.

The cylinder-shaped axial impeller 3 is arranged in the hollow body, wherein FIG. 4 additionally, by way of example, shows the covering of a part of the impeller by the spiral-shaped outlet channel. The spiral-shaped outlet channel 11 runs tangentially to the impeller 3, runs out into the outlet 6 and in this manner forms a spiral chamber (spiral housing).

Figure 5:
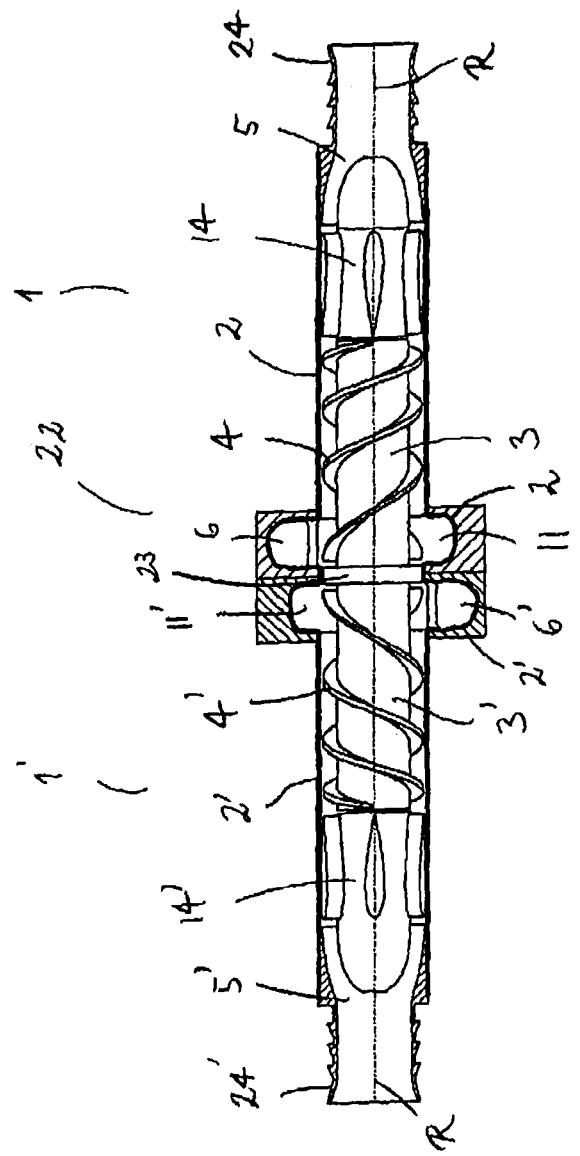

One embodiment of a total heart pump 22 of the type suggested here is schematically represented in FIG. 5. It comprises two blood pumps 1, 1' of the type suggested here, whose hollow bodies 2, 2' are connected axially into a common hollow body. This at its two ends comprises two inlets 5, 5' for the inflow of blood from the pulmonary circulation or the systemic circulation, so that the right blood pump 1 is envisaged as an RVAD and the left blood pump 1' as an LVAD. The two impellers 3, 3' of the two blood pumps 1, 1' are axially connected to one another in a fixed manner into a common impeller. The blood may be driven in an axial manner by way of a suitable design of the blading 4, 4' of the common impeller 3, 3', towards a middle of the common hollow body 2, 2', at which two spiral-shaped outlet channels 11, 11' (spiral chambers) are formed, which in each case run out into an outlet 6, 6' for the tangential (right-angled) outflow of the blood out of the common hollow body 2, 2'.

The blading 4, 4' of the impeller is designed for producing two different values of the blood pressure at the two outlets 6, 6'. The pitch of the spiral-shaped blading is correspondingly adapted for this purpose.

The design parameters of the left pump 1', in particular defining the shape of the impeller 3' and the blading 4' are equal to the design parameters of the blood pumps shown in FIGS. 1-4. The right blood pump 1, however, has an opposite handedness and, moreover, smaller pitch and lead values in order to produce smaller blood pressure values than the left blood pump 1' at same rotational frequency. All other parameters are the same as for the left blood pump 1'. In this example, at the upstream-side of the impeller 3 a local pitch of the blading is about 3 mm and a local lead is about 10 mm. The local pitch and the local lead monotonously increase towards the downstream-side of the impeller 3 to a pitch value of about 8 mm and a lead value of about 25 mm at the downstream-side of the impeller 3, respectively. On average the pitch is about 5 mm and the lead is about 17 mm. At the upstream-side of the impeller 3, a blade angle of the blades is about 80° and monotonously increases towards the end 10 of the impeller to a value of about 55°. On average the blade angle is about 65°.

A connection gap 23 between the common hollow body 2, 2' and the common impeller 3, 3' exists between the two outlet channels 11, 11'. The connection gap 23 may be designed as narrowly as possible in order to reduce a leakage flow of the blood between the cavities 3, 3' of the first and the second blood pump 1, 1'.

Moreover, the total artificial heart, at the two inlets, in each case comprises an olive 24, 24' (connection piece) for the connection of a flexible connection tubing.

Figure 6:
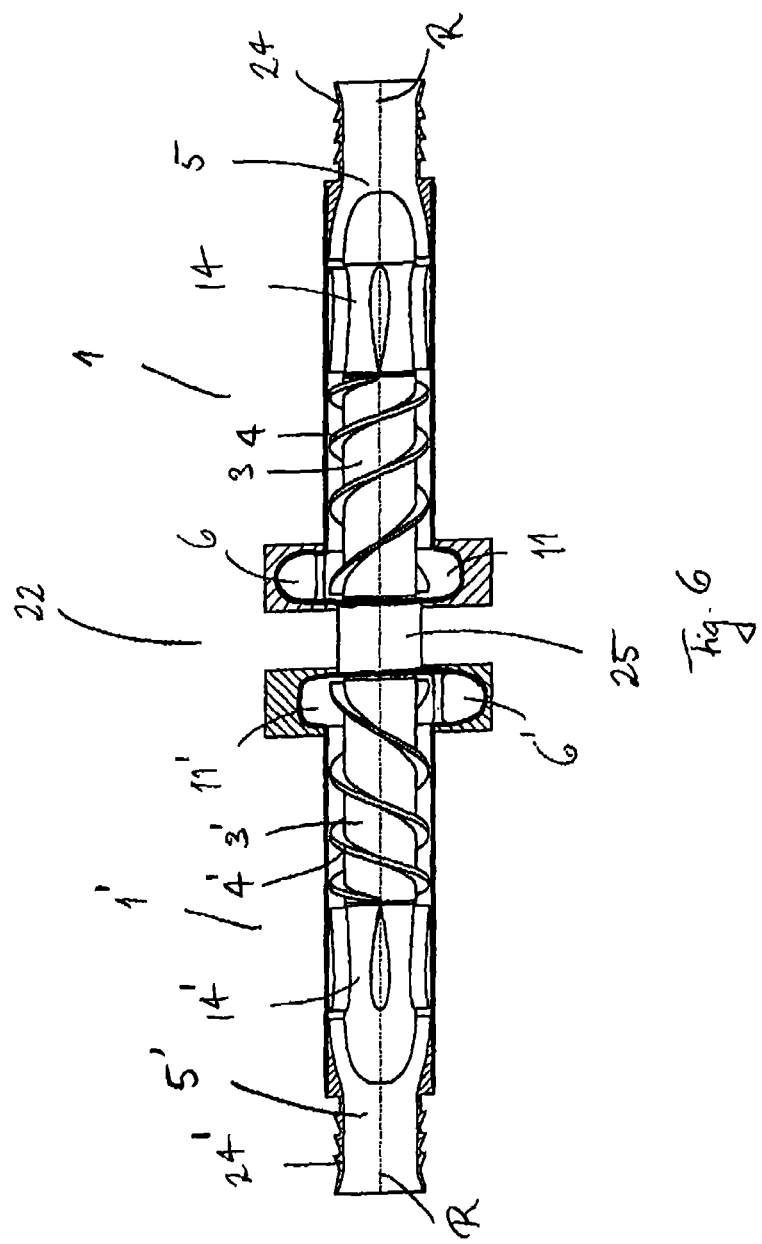

One embodiment of a total artificial heart 2 of the type suggested here, is schematically represented in FIG. 6. It comprises two blood pumps 1, 1' of the type suggested here, whose hollow bodies (cavities) 2, 2' are aligned axially to one another and are connected to one another in a fixed manner via a bearing block 25. The bearing block contains parts of the bearing devices (e.g. permanent-magnetic bearing magnets for the axial bearing) of the two blood pumps 1, 1' for bearing the two impellers 3, 3'. These are not mechanically connected to one another and thus may be rotated about the common rotation axis R independently of one another. The two inlets 5, 5' are envisaged for the flow of blood from the pulmonary circulation or the systemic circulation, so that as in the previous embodiment example, the right blood pump 1 is envisaged as an RVAD and the left blood pump 1' as an LVAD. The blood may be axially driven in the direction of the bearing block 25 by way of a suitable choice of the rotational speed and/or by way of a different design of the blading 4, 4' of the two impellers 3, 3'.

The design parameters of the left pump 1' and the right pump 1, in particular defining the shape of the impeller 3' and 3 and the blading 4' and 4 are equal to the design parameters of the blood pumps shown in FIGS. 1-4.

Moreover, spiral-shaped outlet channels 11, 11' (spiral chambers) are provided in each case at the downstream-sides 10, 10' of the two impellers 3, 3' and these outlet channels in each case run out into an outlet 6, 6' for the tangential (right-angled) flow of blood out of the cavities 2, 2'.

As described above and shown in FIGS. 5 and 6, the downstream-sides oft the impellers 3, 3' of the total artificial hearts 22 shown are facing towards each other so that the blood is pumped towards a center of the total artificial hearts 22 located between the impellers 3 and 3', i.e. the blood is pumped towards the connection gap 23 (FIG. 5) or towards the bearing block 25 located between the two hollow bodies 2, 2' (FIG. 6). So the orientations of the axial propulsion of the two blood pumps 1, 1' of the total artificial hearts 22 are anti-parallel and, directed towards each other.

The invention claimed is:

1. A blood pump, comprising a hollow body, in which an impeller with a blading is provided for an axial propulsion of the blood along the impeller, as well as an at least partly actively stabilised magnetic bearing device for the impeller, wherein the impeller is configured to be set into a rotation about a rotation axis of the impeller with a motor stator located outside the hollow body, and wherein the hollow body includes a hollow cylinder in which the blading is provided, and the hollow body comprises an inlet for the flow of blood into the hollow body in an inflow direction which is essentially parallel to the rotation axis, and an outlet for the outflow of the blood out of the hollow body in an outflow direction, wherein the outlet is arranged offset to the rotation axis of the impeller such that an outflow angle ($\alpha$) is produced between the inflow direction and the outflow direction, said angle being different from zero, and wherein the blading is designed as a helix, and the blading extends along the impeller up to but not past an outlet-side end of the hollow cylinder that is opposite an inlet-side end of the hollow cylinder.

2. A blood pump according to claim 1, wherein an inner radius (r) of the hollow body is enlarged for forming a discharge channel which runs tangentially around the impeller and runs out into the outlet, for a flowing-away of the blood out of the hollow body, running essentially tangentially to the impeller.

3. A blood pump according to claim 2, wherein the discharge channel widens towards the outlet.

4. A blood pump according to claim 1, further comprising an inlet guide vane.

5. A blood pump according to claim 4, wherein the magnetic bearing device is partly integrated into the inlet guide vane.

6. A blood pump according to claim 1, further comprising a hydrodynamic bearing device.

7. A blood pump according to claim 6, wherein the hydrodynamic bearing device of the impeller is designed as a support ring which is connected to the impeller, for forming an annular gap between the support ring and an inner wall of the hollow body, for a radial bearing of the impeller.

8. A blood pump according to claim 1, wherein the outlet of the hollow body is arranged between an upstream-side of the impeller, said upstream-side facing the inlet, and a downstream-side of the impeller, said downstream-side being away from the inlet.

9. A blood pump according to claim 1, wherein the magnetic bearing device has an actively stabilised axial bearing.

10. A blood pump according to claim 1, wherein a peripheral surface of the impeller, said peripheral surface carrying the blading, is designed in an essentially cylinder-shaped manner, cone-shaped manner or truncated-cone-shaped manner.

11. A blood pump according to claim 1, wherein a pitch of the blading lies in a range between 2 mm and 20 mm along an entire axial extent of the blading.

12. A blood pump according to claim 1, wherein a pitch of the blading at a upstream-side of the impeller lies in a range between 2 mm and 8 mm and a pitch of the blading at a downstream-side of the impeller lies in a range between 10 mm and 20 mm.

13. A blood pump according to claim 1, wherein the blading comprises at least one spiral-shaped blade which is wound at least once around the impeller.

14. A blood pump according to claim 1, wherein a maximal height of the blading is less than 50% of a maximal total radius (r') of the impeller.

15. A blood pump according to claim 1, wherein a maximal width of the blading is less than 10% of a maximal total circumference ($2\pi r'$) of the impeller.

16. A blood pump according to claim 1, wherein the blading is spread over at least 80% of an axial length of the impeller.

17. A blood pump according to claim 1, wherein the impeller has a maximal total diameter (2r') which is not larger than 60% of the total axial extent of the blading of the impeller.

18. A blood pump according to claim 1, wherein the partly actively stabilised magnetic bearing device includes an active axial bearing device and a passive radial bearing device.

19. A blood pump comprising: a hollow body comprising a hollow cylinder in which an impeller with a blading is provided for an axial propulsion of the blood along the impeller through the hollow cylinder, wherein the impeller is configured to be set into a rotation about a rotation axis of the impeller with a motor stator located outside the hollow body, and wherein the hollow body comprises an inlet for the flow of blood into the hollow body in an inflow direction which is essentially parallel to the rotation axis, and an outlet for the outflow of the blood out of the hollow body in an outflow direction, wherein the outlet is arranged offset to the rotation axis of the impeller such that an outflow angle ($\alpha$) is produced between the inflow direction and the outflow direction, said angle being different from zero, wherein an inner radius (r) of the hollow body is enlarged to form a spiral-shaped discharge channel which runs tangentially around the impeller and runs out into the outlet, for a flowing-away of the blood out of the hollow body, running essentially tangentially to the impeller, wherein the outlet of the hollow body is arranged between an upstream-side of the impeller, said upstream-side facing the inlet, and a downstream-side of the impeller, said downstream-side being away from the inlet, and wherein the blading is designed as a helix, the blading of the impeller is provided in the hollow cylinder, and the blading does not extend past an outlet-side end of the hollow cylinder that is opposite an inlet-side end of the hollow cylinder.

20. A blood pump according to claim 19, wherein a mechanical, hydrodynamic, a magnetic, or a hybrid bearing device is provided for bearing the impeller.

21. A blood pump according to claim 19, or 20, wherein on a peripheral surface of the impeller, said peripheral surface carrying the blading, is designed in an essentially cylinder-shaped manner.

22. A total artificial heart comprising: two blood pumps according to claim 1, 19, or 20.

23. A total artificial heart according to claim 22, wherein the impellers of the two blood pumps are arranged on a common rotation axis.

24. A total artificial heart according to claim 22, wherein the orientations of the axial propulsion of the two blood pumps are anti-parallel and directed towards each other.

25. A blood pump comprising: a hollow body comprising a hollow cylinder, in which an impeller with a blading is provided for an axial propulsion of blood along the impeller, as well as an at least partly actively stabilised magnetic bearing device and a passive radial bearing device for the impeller, wherein the impeller is configured to be set into a rotation about a rotation axis of the impeller, with a motor stator located outside the hollow body, and wherein the hollow body comprises an inlet for the flow of blood into the hollow body in an inflow direction which is essentially parallel to the rotation axis, and an outlet for the outflow of the blood out of the hollow body in an outflow direction, wherein the outlet is arranged offset to the rotation axis of the impeller such that an outflow angle ($\alpha$) is formed between the inflow direction and the outflow direction, said angle being different from zero, and wherein the blading is designed as a helix, the impeller is located in the hollow cylinder, and the blading extends along a length of the impeller to, but not past, an outlet-side end of the hollow cylinder that is opposite an inlet-side end of the hollow cylinder.

* * * * *